Figure 1A:
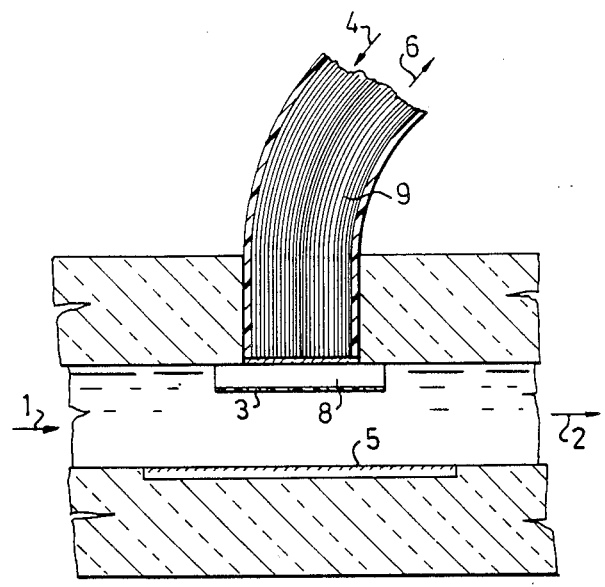

United States Patent [19]

Hansen et al.

[11] Patent Number: 4,973,561
[45] Date of Patent: Nov. 27, 1990

[54] METHOD FOR NON-SEGMENTED CONTINUOUS FLOW ANALYSIS BASED ON THE INTERACTION OF RADIATION WITH A SOLID MATERIAL SITUATED IN A FLOW-THROUGH CELL

[75] Inventors: Elo H. Hansen, Lyngby; Jaromir Ruzicka, Holte, both of Denmark

[73] Assignee: Bifok AB, Sollentuna, Sweden

[21] Appl. No.: 214,307

[22] Filed: Aug. 11, 1988

Related U.S. Application Data

[63] Continuation of Ser. No. 825,208, Feb. 3, 1986, abandoned.

[51] Int. Cl.$^5$ .................. G01N 21/53; G01N 35/08
[52] U.S. Cl. .................. 436/52; 250/432 R; 250/343; 356/436; 356/440; 422/81; 422/83; 436/172; 436/178
[58] Field of Search .................. 436/52, 172, 178; 422/52, 81, 83; 250/432 R, 343; 356/436, 440

[56] References Cited

U.S. PATENT DOCUMENTS

| | | | |
|---|---|---|---|
| 4,003,707 | 1/1977 | Lübbers et al. | 436/68 X |
| 4,224,033 | 9/1980 | Hansen et al. | 422/82 X |
| 4,269,516 | 5/1981 | Lubbers et al. | 356/39 X |
| 4,315,754 | 2/1982 | Ruzicka et al. | |
| 4,504,443 | 3/1985 | Hansen et al. | 436/52 X |
| 4,597,298 | 7/1986 | Ruzicka et al. | 73/863.71 |

FOREIGN PATENT DOCUMENTS 0081116 11/1982 European Pat. Off. .
0126600 5/1984 European Pat. Off. .

Primary Examiner—Robert J. Warden
Assistant Examiner—Jill Johnston
Attorney, Agent, or Firm—Poms, Smith, Lande & Rose

[57] ABSTRACT

One or more components are determined in a sample by bringing said sample, which can be a liquid or a gas, into contact with a medium for adsorbing or taking up the components in question. A light beam is led via an optical cable through the medium containing the adsorbed or taken-up compound sought for, is reflected against a reflector material back through the medium, and the emitted light beam is detected. In enzymatic reactions, inter alia, a membrane can be utilized between sample solution and reagent, said membrane enabling the actual component to diffund through the membrane and react with enzyme, avoiding thereby the measurements to be disturbed by strong coloration and/or a high content of impurities in the sample solution. The membrane thereby serves as a reflector material for the light beam.

12 Claims, 2 Drawing Sheets

METHOD FOR NON-SEGMENTED CONTINUOUS FLOW ANALYSIS BASED ON THE INTERACTION OF RADIATION WITH A SOLID MATERIAL SITUATED IN A FLOW-THROUGH CELL

This application is a continuation of application Ser. No. 06/825,208, filed Feb. 3, 1986 now abandoned.

The present invention relates to serial analysis of discrete samples or to a process control method by means of which a well-defined volume of liquid in the form of a dispersed zone is transported through a flow cell by means of a non-segmented carrier liquid stream. Within said cell there is placed an insoluble solid material reflecting, absorbing or re-emitting an incident radiation, usually in the visible or ultraviolet region. The passage of the sample zone causes, due to one or several chemical reactions, a change in the reflectance, absorbance or emission of radiation on the surface or in the solution in the proximity of said surface of said solid material. The change in intensity of the reflected, absorbed or emitted radiation is then measured by conventional means and converted into a readout. After calibration by means of known standard solutions, the system is readied for assay of unknown samples. Said samples may be part of a series of discrete samples to be analysed, e.g. glucose in blood from different patients, or soil extracts the pH of which is to be measured, or fertilizers to be assayed for ammonia content. Alternatively, the sample zones can be periodically removed from a container or a flowing stream, such as a fermentation tank or a continuous flow reactor, with the aim to periodically control the pH, glucose, oxygen or carbon dioxide contents for monitoring purposes.

Sampling, injection of the zone, control of its dispersion, forward movement, stopping of a selected section of the dispersed sample zone within a detector, and use of these means for serial assay have been described in a number of our U.S. patents, e.g. U.S. Pat. No. 4,224,033. The method of solution transport and sample zone treatment will be referred to below as flow injection analysis (FIA).

Figure 1B:
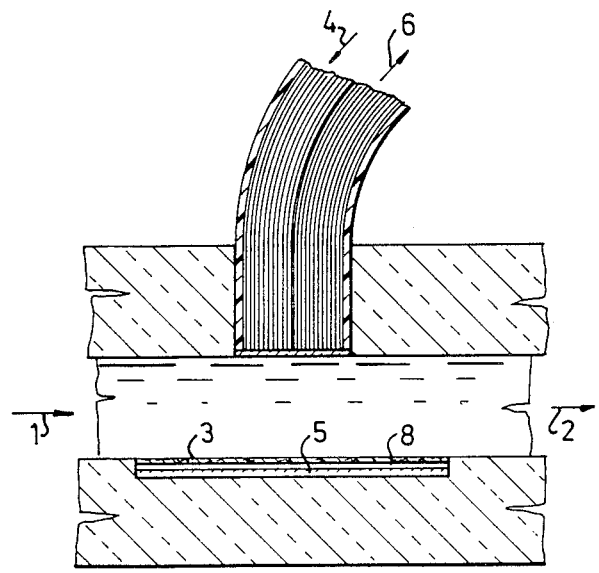
Figure 2:
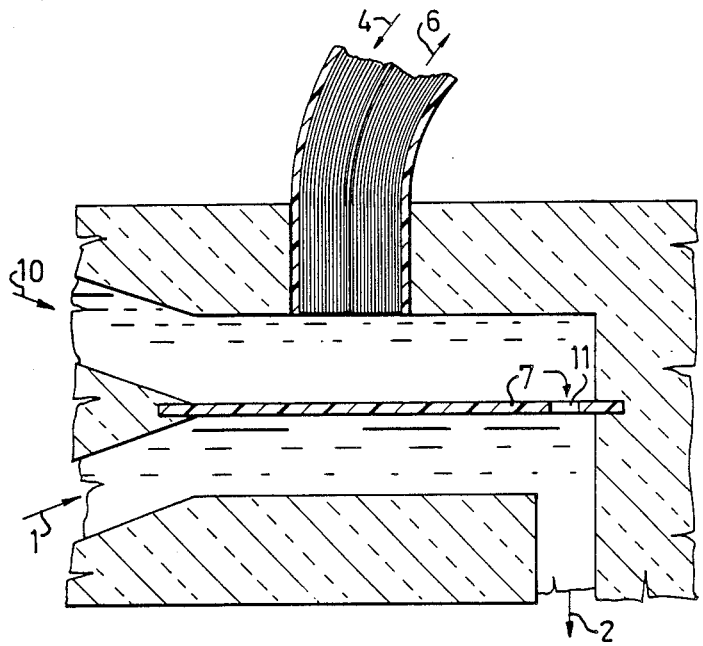

The invention will be more closely described with reference to the accompanying drawings, of which FIGS. 1A and 1B illustrate a measuring apparatus where the medium consists of a solid material and FIG. 2 illustrates a measuring apparatus where the medium is a liquid or a gas.

A sample solution is fed into a flow cell, and after measurement and possible reactions, the outlet 2 is discharged from the cell. On its way through the cell, the sample is passed through a medium 3 which adsorbs or reacts with one or more of the components in the sample. The medium 3, with or without an intermediate carrier 8, is in abutting contact with the end of a bundle of optical fibers 9. Light 4 is led through a portion of this fiber bundle for passage through the carrier 8, the medium 3 and the sample solution to be reflected against a reflector material 5 and a lead back through the sample solution, the medium 3 and the carrier 8 as a light beam 6 to a sensor.

The adsorbent or reagent medium 3 may also be arranged on the reflector material 5 with or without an intermediate carrier layer 8, as is shown in FIG. 1B.

As is the case with the first-mentioned embodiment, the light is thereby passed twice through the medium 3, and for this reason the measuring result will be substantially greater than after one single passage.

Measurement combined with dialysis or gas diffusion is shown in FIG. 2. Sample solution is led into the cell past a membrane 7 and out at 2. Reagent solution 10 is led in on the other side of the membrane and out of the cell, preferably via an opening 11 at the far end of the membrane, and further to the sample outlet 2. In this manner, pressure differences between the two membrane sides will be equalized. If no such pressure equalization is needed, the reagent solution can instead be led out through a separate outlet. The reagent solution then acts as a medium for the reaction or taking-up of material passing through the membrane. This performance can be most economically advantageous and efficient in process control where expensive reagents such as enzymes must be utilized. If the reagent solution then consists of a carrier stream with injected reagent plugs, the consumption of chemicals can be held very low even in case of a continuous, lengthy process control. The reflection of light occurs here against the membrane 7.

The novel feature of the present invention is the use of solid material in a flow cell operated in an FIA instrument. The discussion of interaction of radiation with the solid material will be limited to examples describing changes of reflectance of visible light, but it should be understood that the same principle will apply to absorption of radiation and re-emission of radiation (fluorescence or chemiluminiscence) of visible or ultraviolet light.

The solid material in the flow cell, responding to the changes of composition of the non-segmented carrier stream, caused by the passage of the sample zone, can be arranged in the flow cell as:

(a) a porous structure optionally composed of interwoven fibres;

(b) a non-porous polymer layer;

(c) a porous hydrophobic polymer made membrane separating two layers of liquid;

(d) layered structures of gelatine based materials.

The above structures will comprise colour indicators, enzymes, substrates, buffering and other auxiliary substances which will undergo chemical reactions on which the respective chemical assays will be based. At least some of these compounds in the above structure will have to be immobilized on the surface of said solids. The method of immobilization will have to be designed in such a way that the immobilized materials will remain attached to the surface of said solids for sufficiently long periods of time to warrant reproducible measurement for a period of at least one day. The covalent bonding is one of the most suitable techniques for this purpose. In one case, the use of porous polymer membrane (c), the immobilization is not necessary, being replacable by a periodic renewal of required chemicals (indicator, buffer, enzyme), and this case is therefore treated separately.

The used of immobilized reagents on the surface of reflecting solids has recently reached a new stage of development. The centuries old idea of lithmus paper has been broadened in scope to encompass, besides pH measurements, also measurements of clinically important species like glucose, urea, etc. Another advance, the covalent binding of indicators on the matrices (a) to (d) has resulted in production of homogenous, "non-bleeding" indicators as well as diagnostic aids (sticks) produced by Ames Co (Clinistix, Seralyzer ®) by Boehringer (Refloma ®) and by Kodak (Ektachem ®)

system). The latter system utilizes layered gelatine based structures.

These indicator strips, furnished with a reference scale, are used for semi-quantitative measurement by dipping the strip into a test solution and then placing it into a reflectance measuring instrument.

Thus, for each assay a new strip has to be used, and since the measuring geometry within the reflectance photometer is difficult to reproduce, the measurements are less reproducible than by other automated methods. There are additional reasons why the method of manual handling of said strips is not satisfactory. The amount of liquid applied differs from one sample to the next, and so does the diffusion of sample material into the layer of solid material. Coloured reference bars can never serve as well as standards of real reference solutions (such as standard glucose solutions, pH standard buffers), which would be useful only if the same strip would be first calibrated and then used for assay. Since all manipulations would have to be done manually, the simplicity of operation would suffer. To conclude, manual, batchwise operation is a limiting factor in using these materials. Continuous flow operation based on the FIA principle will improve the reproducibility of measurement and will increase the sampling frequency and operator convenience.

FIA is a sample handling technique that offers a variety of possibilities.

(a) The sample is injected as a plug, the dispersion of which can be controlled by selecting different flow rates, coil lengths, coil diameters, etc;

(b) The sample material is in contact with the detection flow cell during a precise and reproducible time which allows measurements at non-steady state conditions;

(c) The system can be calibrated by reacting standards in the same way as samples;

(d) Samples can be diluted, filtered, pre-concentrated or chemically modified by the aid of reactors (like ion exchange);

(e) The system is conditioned between samples (standards) through the continuously streaming carrier;

(f) The indicator substance in the flow cell is conditioned by the carrier after a sample exposure;

(g) A high sampling throughput can be achieved since the sample residence time is short and steady state is not required;

(h) The sensitivity of the method can be controlled by sample dilution or by prolongation of the reaction time through the stopped-flow technique;

(i) Conditioning of the system can be improved by intermittent pumping of cleaning carrier.

Another aspect of the present invention is microminiaturization of the flow system which will decrease reagent and sample consumption and increase ruggedness of the flow and detector system. This aspect is best illustrated by example of gas diffusion which represents the case of a porous hydrophobic membrane separating two liquids. One of the liquids is a donor stream, i.e. a non-segmented carrier stream transporting the dispersed sample zone. On the other side of the polymer made gas permeable membrane serving as a reflecting solid, the other liquid is situated. This stream, the acceptor stream, contains an indicator which changes colour, and the intensity of the reflected light from said porous membrane, if a volatile species originating from the injected sample zone penetrates the membrane, is measured; the reflected light being related to the colour of the indicator and hence the amount of gas penetrating the membrane. One example of such a system is the measurement of ammonia. At pH values of above 11 in the donor stream, ammonia will diffuse through the porous membrane into the acceptor stream. The amount of ammonia diffusing through the membrane in the described manner will cause a pH change of the acceptor solution and thereby also a change in colour of the acid-base indicator. Similarly, in an assay of carbon dioxide in blood or fermenting liquids the carbon dioxide, which penetrates the porous membrane, will decrease the pH of the acceptor stream thus changing the colour of the acid-base indicator contained within it. Yet, in another assay, oxygen measurement, the oxygen emanating from the liquid sample zone will penetrate the porous membrane and oxidize a coloured soluble species (redox indicator of e.g. vanadium (II)) thus changing the intensity of light reflected from the membrane surface. It is noteworthy that, in these configurations, the reagent used does not have to be immobilized, but may be renewed immediately prior to and after each measuring cycle, that is prior to and after the passage of each sample zone. This approach ensures perfectly reproducible conditions for each measuring cycle and reproducible baseline (i.e. zero content) conditions. Since the volume of acceptor stream in the vicinity of the reflecting membrane is very small (typically less than 5 microliters), the consumption of reagent for each cycle is about one hundred times smaller than for conventional analysis of this type.

The renewal or regeneration principle, so well and reproducibly executable by FIA, can be advantageously applied also when using materials (a), (b) and (d) (pages 3 and 4), if some of the components could not be satisfactorily immobilized.

Yet another important feature of FIA, the stopped-flow approach, is extremely well suited for reproducible operation of detectors containing solid material. Inevitably, all solid porous structures rely heavily on diffusion controlled transport and consequently on exact timing of all operations such as contact times of liquids, concentration gradients, diffusion within the porous structure and rediffusion of reaction products. By holding the dispersed sample zone in contact with the surface of said solids during a prolonged, yet well-defined period of time, the extent of colour formation, gas diffusion, and removal of products prior to the next measuring cycle can be perfectly controlled, thus allowing optimization of signal within the desired concentration range. For illustration, two basic embodiments are shown. FIG. 1A and FIG. 1B represent a flow cell containing a fibrous material with a covalently bound indicator on its surface. FIG. 2 represents a flow cell design containing a gas permeable porous light reflecting membrane, situated between the acceptor solution and the indicator solution. The flow cells have been manufactured as layered structures and integrated into microconduits by a technique described in our U.S. patent application No. 473,227. The microconduits with integrated optical fibres became an ideal vehicle for this purpose. Bifurcated multistrand optical fibre has been used for cell illumination and for collection of the reflected light. The other end of the fibre (not shown), bifurcated into two arms, has been connected to a conventional light source and to a conventional spectrophotometer, which measured the reflected light at a selected wavelength.

More specifically, in the method for measurement of pH, was used a flow cell according to FIG. 1A or 1B, with a covalently bound mixture of bromthymolblue and thymol blue on cellu- lose. The carrier stream consisting of $10^{-4}$ M HCl was pumped at a rate of "1 ml/min, while samples injected (volume 25 microliters) used for calibration consisted of standard buffer solutions within pH 4.0 to 10.0. When measuring reflectance at 620 nm (blue colour) a linear response was obtained within pH 5 to 8, while a useful response was obtained within pH 4 to 9. Sampling frequency was 180 s/h and the same pad of fibrous material could be used continuously for at least four weeks without any deterioration of the response slope or any significant change in baseline position. If the range was limited to pH 7 to 8 and the carrier stream adjusted to pH 6.8 (phosphate buffer), reproducibility of measurement of ±0.005 pH units was obtained.

Measurement of ammonia within the range 1-20 ppm NH was effected by injecting into the donor carrier stream ($1.10^{-3}$ M phosphate buffer of pH 6.5) two adjacent zones consisting of ammonium chloride (35 μl) and 0.1 M sodium hydroxide (21 μl) which upon injection chased each other, thereby in the overlapping part of the two gradients forming an alkaline milieu where ammonia is released. Upon entering into the flow cell (FIG. 2), the ammonia gas diffuses through the porous membrane thereby causing the colour of the acid-base indicator, present in the acceptor stream, to change, which change is monitored by the optical system. In order to increase the sensitivity, a selected segment of the sample zone may be arrested in the flow cell, thereby allowing more ammonia gas to diffuse through the membrane and thus influencing the intensity of the colour change of the indicator. For any preselected stop time there is propotionality between the concentration of ammonia—and hence ammonium chloride in the sample—and the recorded signal. Furthermore, by changing the delay time for the beginning of the stop period, i.e. the point on the gradient of the injected sample zone which is selected for quantification, the sample may be diluted electronically at will.

Measurement of urea in the range 1-10 mmol/l was also effected with the system shown in FIG. 2. The FIA manifold was much similar to the one described for ammonia, except that the sample zone now consisted of urea (volume 25 μl) and the reagent (volume 36 μl) consisted of urease (50 U/ml) dissolved in TRIS-buffer (0.1 M, pH 8.32), while the carrier stream was 0.1 M TRIS-buffer (pH 8.32). During the passage to the flow cell, urea is degraded enzymatically by urease to ammonia, which is measured as before, again using a stop sequence to enhance the sensitivity. Standard deviation was for ±0.3% and the system functioned for several months of operation. Alternatively, the injected sample zone of ure may be degraded to ammonia on its way towards the detector via passage of a column reactor containing immobilized urease.

We claim:

1. An apparatus for conducting continuous flow analysis for the determination of a substance in a sample comprising:
    a flow cell having an inlet for receiving a continuous flow of a carrier stream having discrete sample plugs carried therein, said flow cell further including a passageway for said carrier stream to pass through said flow cell and an outlet connected to said passageway through which said carrier stream flows from said flow cell;
    a solid indicator medium located in said passageway for direct contact with said carrier stream, said indicator medium being capable of allowing radiation to pass therethrough and wherein said indicator medium interacts with said substance to be determined, said interaction producing a change in a measurable characteristic of said indicator medium;
    measurement means for measuring said change in said measurable characteristic wherein said measurement means comprises:
    means for directing radiation onto a first side of said indicator medium wherein at least a portion of said radiation passes through said indicator medium and emerges from a second side of said indicator medium;
    a reflector for reflecting the radiation which emerges from said indicator medium second side back through said indicator medium; and
    means for measuring changes in said radiation after said radiation has been directed onto the first side of said indicator medium.

2. An apparatus according to claim 1 wherein said indicator medium interacts with said substance by absorption or reaction.

3. An apparatus according to claim 1 wherein said reflector is located adjacent to said second side of said indicator medium.

4. An apparatus according to claim 3 wherein said indicator medium is located in said passageway so that said radiation is directed through said carrier stream prior to reaching said indicator medium.

5. An apparatus according to claim 3 wherein a carrier layer is placed between said indicator medium and said reflector.

6. An apparatus according to claim 1 wherein said indicator medium and said reflector are located on opposite sides of said passageway.

7. An apparatus according to claim 1 wherein said radiation is light.

8. A method of continuous flow analysis for the determination of a substance in a sample comprising the steps of:
    flowing a carrier stream through a passageway in a flow cell, said carrier stream having discrete sample plugs carried therein;
    directly contacting said carrier stream with a solid indicator medium located in said passageway, wherein said indicator medium interacts with said substance to be determined, said interaction producing a change in a measurable characteristic of said indicator medium and wherein said indicator medium is capable of allowing radiation to pass therethrough;
    measuring the change in said measurable characteristic due to the interaction of said substance with said indicator medium wherein said measuring comprises the steps of:
    directing radiation onto a first side of said indicator medium wherein at least a portion of said radiation passes through said indicator medium and emerges from a second side of said indicator medium;
    reflecting the radiation which emerges from said indicator medium second side back through said indicator medium; and measuring changes in said radiation after said radiation has been directed onto the first side of said indicator medium.

9. A method of continuous flow analysis according to claim 8 wherein said indicator medium interacts with said substance by absorption or reaction.

10. A method of continuous flow analysis according to claim 8 wherein said reflector is located adjacent to said second side of said indicator medium.

11. A method of continuous flow analysis according to claim 8 wherein said indicator medium is located in said passageway so that said radiation is directed through said carrier stream prior to reaching said indicator medium.

12. A method of continuous flow analysis according to claim 8 wherein said indicator medium and said reflector are located on opposite sides of said passageway.

* * * * *